(12) United States Patent
Lorang et al.

(10) Patent No.: US 8,956,347 B2
(45) Date of Patent: *Feb. 17, 2015

(54) ELECTROSURGICAL POWER CONTROL

(71) Applicant: Smith & Nephew, Inc., Memphis, TN (US)

(72) Inventors: Douglas M. Lorang, Ripon, CA (US); Matthew E. Mitchell, Pelham, NH (US); Karen Drucker, Danville, NH (US); Kobi Iki, San Carlos, CA (US)

(73) Assignee: Smith & Nephew, Inc., Memphis, TN (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/090,223

(22) Filed: Nov. 26, 2013

(65) Prior Publication Data

US 2014/0088589 A1  Mar. 27, 2014

Related U.S. Application Data

(60) Continuation of application No. 13/705,836, filed on Dec. 5, 2012, now Pat. No. 8,603,082, which is a division of application No. 13/242,913, filed on Sep. 23, 2011, now Pat. No. 8,348,934, which is a division of application No. 12/691,610, filed on Jan. 21, 2010, now Pat. No. 8,052,675, which is a division of application No. 11/158,340, filed on Jun. 22, 2005, now Pat. No. 7,655,003.

(51) Int. Cl.
  *A61B 18/18* (2006.01)
  *A61B 18/12* (2006.01)
  *A61B 17/00* (2006.01)
  *A61B 18/00* (2006.01)

(52) U.S. Cl.
  CPC ............. *A61B 18/18* (2013.01); *A61B 18/1206* (2013.01); *A61B 18/1233* (2013.01); *A61B 2017/00026* (2013.01); *A61B 2017/00084* (2013.01); *A61B 2018/00666* (2013.01); *A61B 2018/00678* (2013.01); *A61B 2018/00702* (2013.01); *A61B 2018/00726* (2013.01); *A61B 2018/00791* (2013.01); *A61B 2018/00875* (2013.01)
  USPC .................. 606/32; 606/34; 606/38; 606/39; 606/40

(58) Field of Classification Search
  USPC ......................................... 606/32, 34, 38–40
  See application file for complete search history.

(56) References Cited

U.S. PATENT DOCUMENTS 8,603,082 B2 * 12/2013 Lorang et al. ................... 606/32

* cited by examiner

*Primary Examiner* — Lee S Cohen
(74) *Attorney, Agent, or Firm* — Chapin IP Law, LLC

(57) ABSTRACT

A method and apparatus include determining a value of a parameter associated with operation of an electrosurgical probe having a particular probe design, and determining whether the value of the parameter is within a range of values that has been predetermined for the particular probe design to indicate that the probe is treating tissue in a desired manner. Power is delivered to the probe according to an algorithm based upon a determination that the value of the parameter is outside the range of values The algorithm delivers power in a pulsed profile including portions of low power and portions of high power. In one embodiment, the tissue treatment is ablation, the parameter is impedance, and the method limits tissue necrosis to less than 200 microns. In another embodiment, the tissue treatment is shrinkage, the parameter is temperature, and the method limits power delivery when the probe is not shrinking tissue.

12 Claims, 11 Drawing Sheets

ELECTROSURGICAL POWER CONTROL

CROSS-REFERENCE TO RELATED APPLICATIONS

This application is a continuation of, and claims priority from, U.S. Ser. No. 13/705,836, filed Dec. 5, 2012, now U.S. Pat. No. 8,603,082, which is a divisional application of, and claims priority from, U.S. patent application Ser. No. 13/242,913, filed Sep. 23, 2011, now U.S. Pat. No. 8,348,934, issued Jan. 8, 2013, which is a divisional of U.S. patent application Ser. No. 12/691,610, filed Jan. 21, 2010, now U.S. Pat. No. 8,052,675, issued Nov. 8, 2011, which is a divisional of U.S. patent application Ser. No. 11/158,340, filed on Jun. 22, 2005, now U.S. Pat. No. 7,655,003, issued Feb. 2, 2010. The contents of the prior applications are incorporated herein by reference in their entirety.

TECHNICAL FIELD

This application relates to electrosurgical power control.

BACKGROUND

Radiofrequency (RF) energy is delivered to a surgical instrument, such as a probe, to treat diseased tissue, such as by ablating, shrinking, cutting, or coagulating the tissue. For example, RF energy is used to ablate fibrillations and smooth the surface of articular cartilage that suffers from chondromalacia and osteoarthritis. RF energy also is used to shrink collagen tissue in a joint. The use of RF energy can produce collateral damage in the form of undesired cell death or the excess removal of healthy tissue. For example, in the case of articular cartilage, RF energy can cause the death of chondrocytes, the cells responsible for maintaining cartilage viability and growth, which cannot be regenerated after death.

SUMMARY

In various described embodiments, power delivered to a probe is controlled to treat tissue in a desired manner (e.g., ablating, cutting, shrinking, or coagulating) while also limiting the power delivered to the probe when the probe is not treating tissue in the desired manner (e.g., when the probe is positioned too far from the tissue to achieve the desired tissue effect). Limiting the power may limit undesired surgical outcomes, e.g., by limiting the extent of undesired collateral cell death. In several such embodiments, that value of a parameter associated with operation of the probe (e.g., impedance or temperature) is determined and compared to a range of values for that parameter that has been predetermined, for that particular probe design, to indicate that the probe is treating tissue in the desired manner. For example, an impedance of over 1000 ohms can indicate that a probe is ablating tissue and, for example, a temperature between approximately 75° C. and 85° C. can indicate that a probe is shrinking tissue. If the parameter is outside the range of values for that probe, the probe enters a pulsed power mode to limit the power delivered. By limiting the power delivered when the probe is not treating tissue in the desired manner, the undesired surgical outcome is limited. The range of values for the parameter can vary based on the probe design and the desired manner of treatment.

According to a general aspect, a method includes determining a value of a parameter. The parameter is associated with operation of an electrosurgical probe having a particular probe design. The method includes determining whether the value of the parameter is within a range of values that has been predetermined for the particular probe design to indicate that the probe is treating tissue in a desired manner. The method further includes delivering power to the probe according to an algorithm based upon a determination that the value of the parameter is outside the range of values. The algorithm includes a pulsed profile including portions of low power and portions of high power.

Embodiments may include one or more of the following features.

The parameter may include an impedance. The range of the impedance may be between approximately 50 ohms and approximately 4000 ohms. The desired manner of tissue treatment may include ablation. The low power in the pulsed profile may be limited to a duration that causes substantially no noticeable delay in initiating ablation. The duration of the pulsed low power may be between approximately 50 milliseconds and approximately 500 milliseconds. The low power in the pulsed profile may include a power setting between approximately 0 watts and approximately 50 watts. The high power in the pulsed profile may have a duration substantially equal to a minimum length sufficient to initiate ablation. The high power may include a power setting between approximately 40 watts and approximately 300 watts.

The parameter may include a temperature. The range of the temperature may be between approximately 65° C. and approximately and approximately 90° C. The desired manner of tissue treatment may include shrinkage. The low power in the pulsed profile may be limited to a duration that limits a delay in initiating shrinkage. The low power in the pulsed profile may include a power setting between approximately 0 watts and approximately 20 watts. The high power in the pulsed profile may have a duration that is greater than a time needed for the temperature to reach a lower limit of the range when the probe is shrinking tissue and that is less than a time needed for the temperature to reach a lower limit of the range when the probe is not shrinking tissue. The high power may include a power setting between approximately 10 watts and approximately 300 watts.

Power may be delivered to the probe according to a second algorithm different from the algorithm to treat tissue in the desired manner based upon a determination that the value of the parameter is within the range of values. The method may switch from the algorithm to the second algorithm upon a determination that the parameter is greater than a lower limit of the range of values by a margin. The method may switch from the second algorithm to the algorithm upon a determination that the parameter is less than a lower limit of the range of values by a margin.

A specific number of values of the parameter may be determined. The specific number may be greater than one. For less than all of the specific number of values, it may be determined whether the values of the parameter are within the predetermined range of values.

According to another general aspect, an apparatus includes one or more computer readable media having instructions stored thereon and configured to result in at least the following. A value of a parameter associated with operation of an electrosurgical probe having a particular probe design is determined. Whether the value of the parameter is within a range of values that has been predetermined for the particular probe design to indicate that the probe is treating tissue in a desired manner is determined. Power is delivered to the probe according to an algorithm based upon a determination that the value of the parameter is outside the range of values. The algorithm has a pulsed profile including portions of low power and portions of high power.

According to another general aspect, a method includes making one or more determinations that an impedance value encountered by an electrosurgical probe is less than a threshold value. The method also includes limiting tissue necrosis to less than 200 microns by delivering power to the electrosurgical probe, in response to at least one of the one or more determinations that the impedance is less than the threshold value, according to an algorithm having a pulsed profile of low and high power.

Embodiments may include one or more of the following features.

For example, the method may include limiting the low power in the pulsed profile to a duration that causes substantially no noticeable delay in initiating the ablative mode. The duration of the pulsed low power may be between approximately 50 milliseconds and approximately 500 milliseconds, e.g., approximately 201.5 milliseconds. Limiting tissue necrosis may include providing the high power in the pulsed profile with a duration substantially equal to a minimum length sufficient to initiate delivery of power in an ablative mode. The duration of the pulsed high power may be between approximately 10 milliseconds and approximately 100 milliseconds, e.g., approximately 19.5 milliseconds. Limiting tissue necrosis may also include providing the low power in the pulsed profile between approximately 0 watts and approximately 50 watts, e.g., approximately 10 watts. The threshold value may be between approximately 50 ohms and approximately 4000 ohms, e.g., approximately 1000 ohms.

The method may include checking the impedance value between approximately every 1 millisecond and approximately every 10 milliseconds, e.g., approximately every 6.5 milliseconds, in order to determine if the impedance value is less than the threshold value. The high power may include a power setting between approximately 40 watts and approximately 300 watts, e.g., approximately 60 watts, with a duration between approximately 10 milliseconds and approximately 100 milliseconds, e.g., approximately 19.5 milliseconds. The low power may include a power setting of between approximately 0 watts and approximately 50 watts, e.g., approximately 10 watts, with a duration between approximately 50 milliseconds and approximately 500 milliseconds, e.g., approximately 201.5 milliseconds.

The method may include making one or more determinations that the impedance value encountered by the electrosurgical probe exceeds the threshold value, and delivering power according to a second algorithm in response to at least one of the one or more determinations that the impedance exceeds the threshold value. The second algorithm may include delivering a substantially constant power. The method may include changing from the second algorithm to the pulsed profile in less than approximately 10 milliseconds, e.g., approximately 1 millisecond, after determining that the impedance is less than the threshold value. The method may include changing from the pulsed profile to the second algorithm upon a determination that the impedance exceeds a value between approximately 50 ohms and approximately 4000 ohms, e.g., approximately 1100 ohms. The method may include changing from the second algorithm to the pulsed profile upon a determination that the impedance is less than a value between approximately 50 ohms and approximately 4000 ohms, e.g., approximately 1000 ohms.

According to another general aspect, an electrosurgical probe is configured to deliver power to tissue. A control module is configured to make one or more determinations that an impedance value encountered by the electrosurgical probe is less than a threshold value. The control module is further configured to limit tissue necrosis to less than 200 microns by delivering power to the electrosurgical probe, in response to at least one of the one or more determinations that the impedance is less than the threshold value, according to an algorithm having a pulsed profile of low and high power.

Embodiments may include one or more of the following features. The probe may include the control module. A generator may be configured to provide power to the probe, and the generator may include the control module.

According to another general aspect, a method includes determining whether a probe is delivering power in an ablative mode or a non-ablative mode. Power is delivered according to a first algorithm when in the ablative mode, and power is delivered according to a second algorithm different from the first algorithm when in the non-ablative mode. The second algorithm includes a pulsed profile including portions of low power and portions of high power. The portions of high power are of sufficient durations to initiate the ablative mode and the durations are less than 250 milliseconds.

According to another general aspect, a method includes determining a rate at which a temperature of a probe approaches a range of temperatures that has been predetermined to enable shrinkage of tissue. The method also includes determining whether the rate is within a range of rates that has been predetermined to indicate that a distance from the probe to tissue is small enough to enable shrinkage of tissue at a temperature in the range of temperatures. The method includes delivering power to the probe according to an algorithm based upon a determination that the rate is outside the range of rates, the algorithm comprising a pulsed profile including portions of low power and portions of high power. In an embodiment, the range of rates has been predetermined based on the probe design.

Advantages may include more consistent surgical outcomes despite variations in surgical technique, and improved safety during electrosurgery.

One or more of the general aspects may be embodied in, e.g., a method or an apparatus. The apparatus may include a component configured to perform various operations, functions, or instructions.

The details of one or more embodiments are set forth in the accompanying drawings and the description below. Other features will be apparent from the description and drawings, and from the claims.

DETAILED DESCRIPTION

Figure 1A:
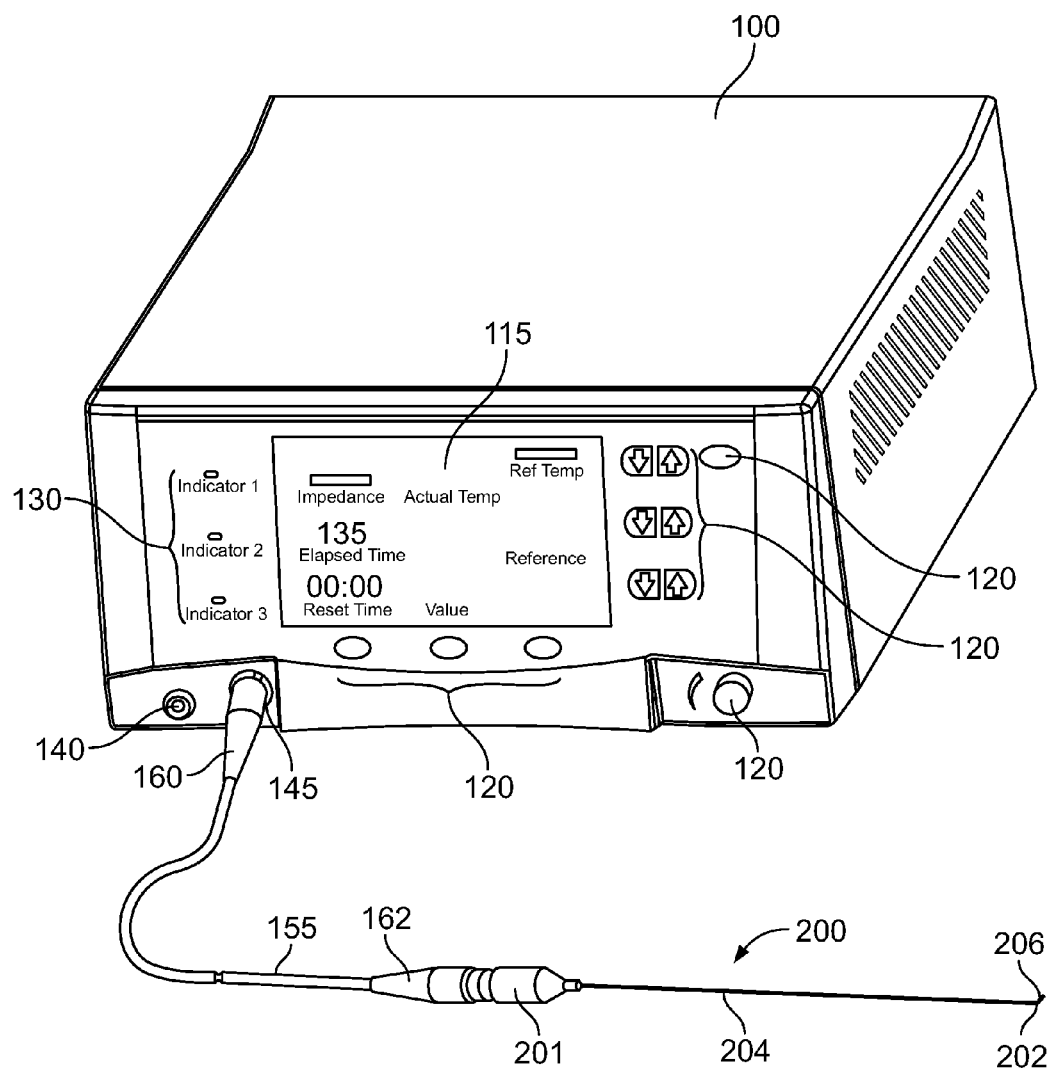
FIG. 1A is an illustration of a system including a generator and a probe.

Referring to FIG. 1A, an electrosurgical probe 200 is coupled to an RF generator 100 to apply RF energy to treat tissue in a desired manner, e.g., to ablate, shrink, cut, or coagulate tissue. Generator 100 can be, for example, a Vulcan® generator sold by Smith & Nephew, Inc., of Memphis, Tenn. (catalog no. 7210812). Generator 100 includes a display 115, control buttons 120, status indicators 130, a receptacle 140 for a grounding pad (not shown), and a receptacle 145 that receives probe 200 via a cable plug 160, a cable 155, and a cable plug 162. Probe 200 includes a handle 201, a shaft 204 extending from handle 201, and an electrode 206 coupled to a distal end 202 of shaft 204 for applying energy to tissue. The instructions for generator controls, as described in greater detail below, can be implemented in hardware or software, can be built into generator 100 or probe 200, and can be stored on one or more computer readable media, such as one or more memory cards.

Delivering power according to a high generator power setting may be required to treat tissue in a desired manner. However, delivering power according to the same high generator power setting when the probe is not operating in the desired manner can contribute to adverse surgical outcomes, such as collateral cell death. As a result, when treating tissue with RF energy, it is desirable to keep the probe operating in the desired manner (e.g., ablating or shrinking tissue) as much as possible, and to avoid delivering high power (e.g., power sufficient to ablate or shrink tissue) when the probe is not operating in the desired manner. Further, when a surgeon moves a probe, e.g., from one portion of tissue to another, the probe's distance to tissue can vary, which can cause the probe to switch between delivering power in the desired manner and delivering power in another manner. To facilitate more consistent surgical outcomes, it is desirable to allow the probe to quickly switch between delivering power in the desired manner and delivering power in another manner when the distance to tissue is varied. In many cases, whether the probe is operating in the desired manner can be determined, on a probe-by-probe basis, by determining a parameter associated with probe operation (e.g., impedance or temperature) and comparing that parameter to a range of values that has been predetermined, for that particular probe design, to indicate that the probe is operating in the desired manner.

Figure 1B:
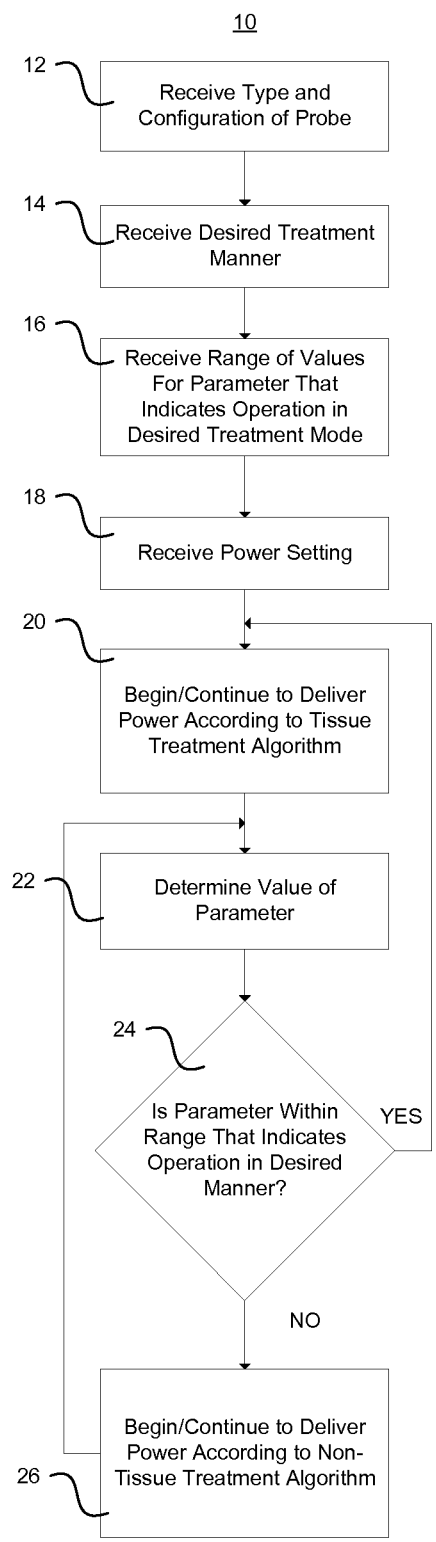
FIG. 1B is a flow chart showing a general power control method used to control power delivery from the generator to the probe of FIG. 1A.

Referring to FIG. 1B, generator 100 controls the power delivered to probe 200 according to an algorithm 10 when probe 200 is used to treat tissue. In typical embodiments, generator 100 initially receives or accesses the type and configuration of the probe being used in the tissue treatment (12), the desired tissue treatment to be performed by the probe (14), a range of values for a parameter (e.g., impedance or temperature) that has been predetermined to indicate that the particular probe is treating tissue in the desired manner (16), and a desired power setting for the probe (18). Additionally, one or more of these inputs may be received implicitly, e.g., by user selection of an algorithm for a particular probe type and configuration, or use of a generator that only supports one probe type and configuration. These inputs also may be received by being built into an algorithm (e.g., range of parameter values or power settings). These inputs can be received, e.g., via manual user input or by automated storage and retrieval of information, according to known methods. These inputs are specific to the probe design and can vary based on the probe being used.

Generator 100 then delivers power to probe 200 according to a tissue treatment algorithm that is designed to deliver power in a manner that allows probe 200 to treat tissue in the desired manner, e.g., by delivering power according to a constant power setting or according to a dynamic control algorithm such as a proportional-integral-derivative (PID) control algorithm (20). In an embodiment, substantially constant power can be delivered according to a dynamic control algorithm that adjusts voltage and/or current to attempt to maintain power While delivering power according to the tissue treatment algorithm, algorithm 10 periodically determines the value of the parameter of interest (22) and compares the determined value of the parameter with the range of values that has been predetermined to indicate that the probe is treating tissue in the desired manner (24). In an embodiment, algorithm 10 determines a specific number of values of the parameter, the specific number being greater than one, and determines, for less than all of the specific number of values, whether the values of the parameter are within the predetermined range of values.

If the determined value of the parameter is within the range of values ("yes" branch from 24), probe 200 is determined to be treating tissue in the desired manner, and generator 100 continues to deliver power according to the tissue treatment algorithm (20). If the determined value of the parameter is outside the range of values ("no" branch from 24), probe 200 is determined not to be treating tissue in the desired manner, and generator 100 switches to delivering power according to a non-treatment algorithm that pulses the power setting between a high power value and a low power value (26). In either case, algorithm 10 continues to periodically determine the value of the parameter of interest (22) and to compare the determined value of the parameter with the range of values that indicates that probe 200 is treating tissue in the desired manner (24). If the determined value of the parameter is within the range of values ("yes" branch from 24), generator 100 delivers power according to the tissue treatment algorithm (20). If the determined value of the parameter is outside the range of values ("no" branch from 22), generator 100 delivers power according to the non-treatment algorithm (26).

Figure 2:
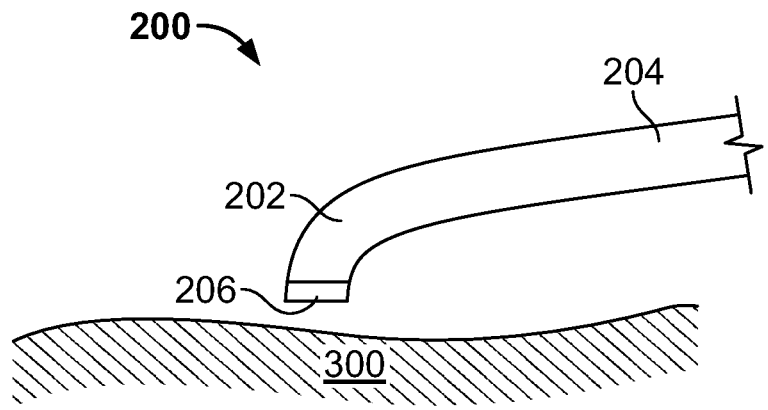
FIG. 2 is a schematic illustration of an embodiment of the probe of FIG. 1A positioned to apply energy to tissue in an ablative mode.
Figure 3:
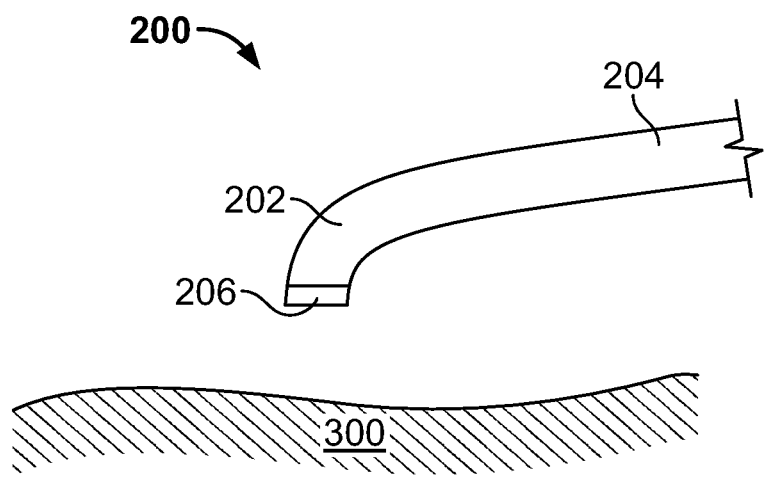
FIG. 3 is a schematic illustration of the probe of FIG. 2 positioned to apply energy to tissue in a non-ablative mode.

Referring to FIGS. 2 and 3, in one embodiment, RF power is delivered from generator 100 to electrode 206 to smooth cartilage tissue 300 by ablation as probe 200 is moved across the surface of tissue 300. Probe 200 is monopolar, such that energy passes from electrode 206, through the tissue 300 and surrounding saline, to a return electrode pad (not shown) attached to receptacle 140 (FIG. 1) and placed elsewhere on the patient. Probe 200 can be, for example, a Glider probe (catalog no. 7210438) or a Sculptor probe (catalog no. 7210697) sold by Smith & Nephew, Inc. In an alternative embodiment, the probe could be bipolar such that a return electrode is located on the probe (not shown).

When probe 200 is placed sufficiently close to or in contact with the tissue surface 300, e.g., approximately 0 mm to approximately 5 mm from the tissue surface 300, as illustrated by the position of probe 200 in FIG. 2 (not to scale), power can be delivered to probe 200 sufficient to ablate the tissue. When probe 200 is ablating tissue, probe 200 is in an "ablative mode." In the ablative mode, an electrical arc or plasma discharge is formed between probe 200 and the tissue and saline such that a light appears to be given off from the probe-tissue interface, and the electrical arc ablates the cells of the tissue.

When probe 200 is moved further away from the tissue surface 300, e.g., at least approximately 0.5 mm to at least approximately 5 mm, as illustrated by the position of probe 200 in FIG. 3 (not to scale), and probe 200 is no longer able to ablate the tissue, the probe is in a "non-ablative mode." In the non-ablative mode, energy from probe 200 heats the fluid surrounding the tissue, which can heat the surrounding tissue to a temperature that causes cell death, an undesired surgical outcome. For example, chondrocyte cells in articular cartilage cells tend to die when raised to a temperature that is greater than approximately 55° C. This can occur, for example, when the surgeon moves probe 200 away from the tissue to reposition probe 200 on the tissue surface while the probe is delivering RF energy.

The ablative mode and the non-ablative mode are characterized by a parameter that has been predetermined, for the design of probe 200, to indicate that probe 200 is operating in, e.g., the ablative mode or the non-ablative mode. In an embodiment, operation in the ablative mode is indicated by an impedance encountered by the probe. For example, an impedance that falls within a range that is greater than a threshold value, e.g., greater than a value between approximately 50 ohms and approximately 4000 ohms, indicates that the probe is determined to be operating in the ablative mode. When the impedance is outside this range, e.g., less than the threshold value, the probe is operating in the non-ablative mode. In another embodiment, a high temperature at probe 200, e.g., greater than approximately 100° C., can indicate that the probe is operating in the ablative mode.

The impedance is higher when the probe is operating in the ablative mode, at least in part, due to the high impedance of the arc/discharge, and to the higher impedance of tissue, as compared to surrounding fluid. Lower impedance indicates operation in the non-ablative mode, at least in part, due to the lower impedance of the surrounding fluid. The impedance threshold that indicates ablation can be determined empirically, e.g., by delivering a constant output power to the probe and determining the impedance when the probe is operating in the non-ablative mode (e.g., by operating the probe in saline) and the impedance when the probe is operating in the ablative mode (e.g., by using the probe to ablate a tissue sample). Operation in the ablative mode is indicated, e.g., by light that appears to be given off from the probe-tissue interface. After several values of impedance in the non-ablative and ablative modes have been determined, a threshold value for the impedance can be computed. A typical threshold indicating operation in the ablative mode may be, e.g., the lowest value of impedance that always (or with a certain degree of confidence) indicates that the ablation is occurring. In another embodiment, the threshold that indicates operation in the ablative mode may be selected, as, e.g., the lowest value of impedance that indicates ablation and that provides a margin of a predetermined size such that the threshold can be decreased by a predetermined size and still indicate ablation.

The threshold value for impedance that indicates probe operation in the ablative mode can vary based on generator design, probe design, and the surgical environment. For example, impedance can vary based on the surface area of the electrode and materials used in construction of the probe. For example, an electrode having a larger surface area may have a lower impedance threshold than a probe with a smaller electrode surface area. Insulating materials of the probe that have poorer dielectric properties can allow more current leakage and reduce the impedance values. Current carrying components of the probe with a lower conductivity can contribute to higher impedance values. In one embodiment, for the Glider probe, the threshold value of the impedance has been predetermined to be approximately 1000 ohms. In another embodiment, for the Sculptor probe, which has a larger electrode surface area than the Glider probe, the threshold value of the impedance has been predetermined to be approximately 700 ohms.

Figure 4:
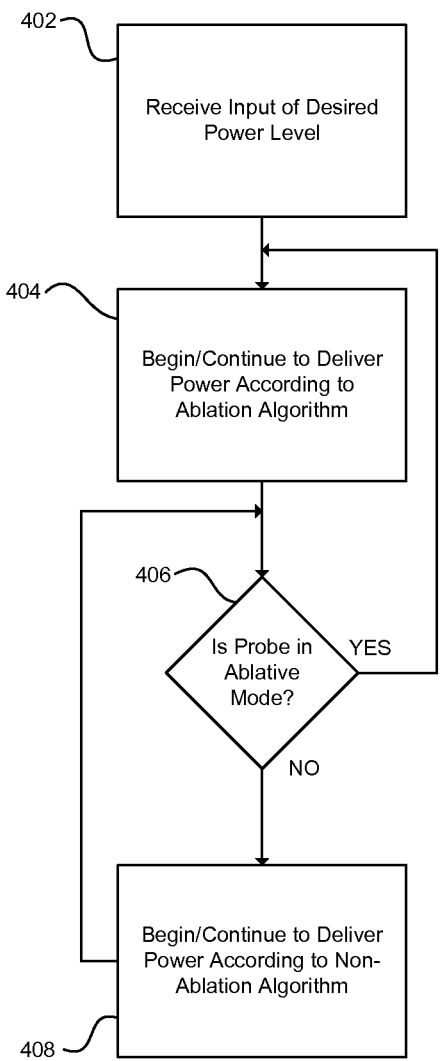
FIG. 4 is a flow chart showing an embodiment of the power control method of FIG. 1B used for ablation of tissue.

Referring to FIG. 4, a first embodiment of a power control algorithm 400 uses ablation and non-ablation algorithms to control the power output to probe 200. Generator 100 receives an input of the desired power level from an operator of probe 200 (402). Generator 100 initially delivers power to probe 200 according to an ablation algorithm that is designed to deliver a power level sufficient to allow probe 200 to operate in the ablative mode, as described in more detail below with respect to FIG. 6 (404). Algorithm 400 then periodically determines, while continuing to deliver power according to the ablation algorithm, whether probe 200 is delivering power in the ablative mode or the non-ablative mode (406). If probe 200 is operating in the ablative mode ("yes" branch from 406), generator 100 continues to deliver power according to the ablation algorithm (404).

If the power control algorithm 400 determines that probe 200 is operating in the non-ablative mode ("no" branch from 406), generator 100 switches to delivering power according to a non-ablation algorithm designed to limit the amount of power delivered to the tissue, as described in more detail below with respect to FIG. 7 (408). Algorithm 400 continues to periodically determine, while continuing to deliver power according to the non-ablation algorithm, whether probe 200 is delivering power in the ablative mode or the non-ablative mode (406) and quickly switches back to the ablation algorithm (404) upon a determination that probe 200 is operating in the ablative mode.

In certain instances, generator 100 may be controlled by the ablation algorithm even though probe 200 is operating in the non-ablative mode, e.g., if there is a lag in algorithm 400 determining that probe 200 has switched to the non-ablative mode. Conversely, in certain instances, generator 100 may be controlled by the non-ablation algorithm even though probe 200 is operating in the ablative mode, e.g., if there is a lag in algorithm 400 determining that probe 200 has switched to the ablative mode. Although the power control algorithm is depicted with the ablation algorithm being the initial setting, in another embodiment the non-ablation algorithm is the initial setting.

Figure 5:
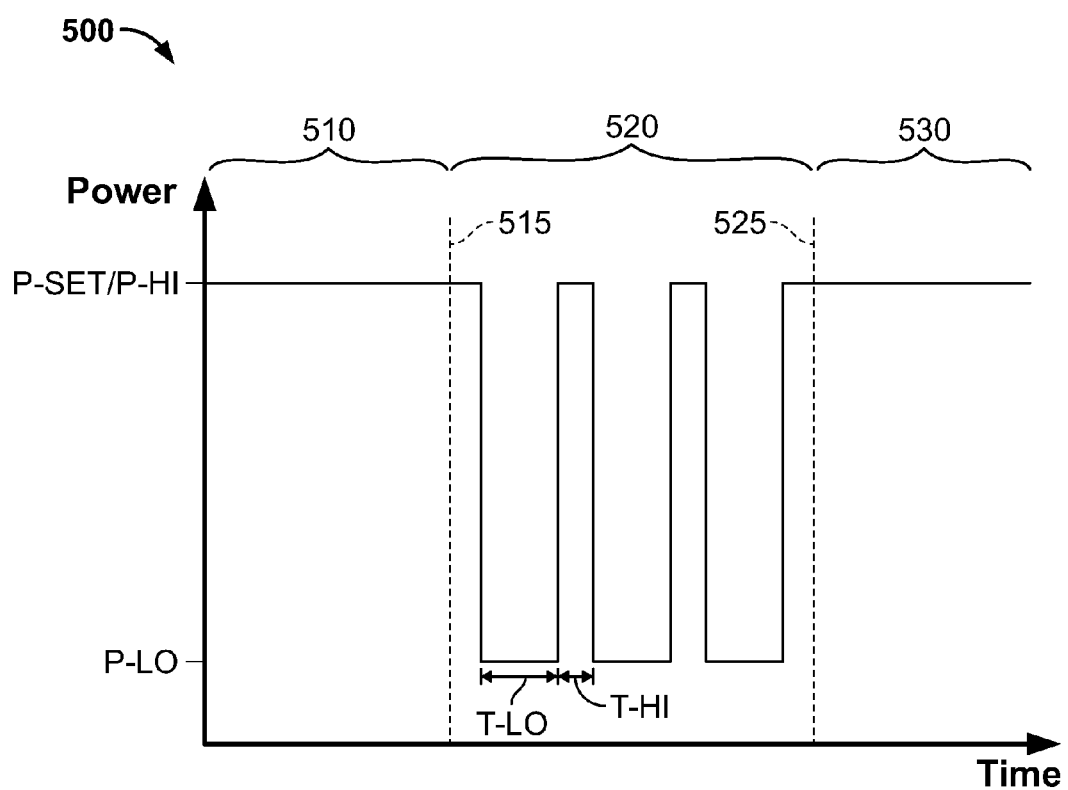
FIG. 5 is a graphical representation of power delivered to a probe by the generator according to the power control method of FIG. 4.

Referring to FIG. 5, power control algorithm 400 causes generator 100 to produce an exemplary power profile 500 having portions 510, 520, and 530 that correspond to the ablation algorithm, the non-ablation algorithm, and the ablation algorithm, respectively. The power levels generated by the ablation and non-ablation algorithms and depicted in FIG. 5 are power settings for generator 100. The output to probe 200 is, e.g., an alternating current waveform in the form of a sinusoidal RF waveform, that can average to a value at or below the power setting. For example, the power can be equal to the time average of the product of the average current, the average voltage, and the cosine of the phase shift between the current and voltage. Also, due to the impedance encountered by probe 200, e.g., from saline or tissue, the average power output from generator 100 and probe 200 can be less than the power setting. For example, for a power setting of 60 Watts, if probe 200 is in saline (low-impedance) the average power output can be, e.g., approximately 50 Watts, and if probe 200 is being applied to tissue (high-impedance), the average power output can be, e.g., approximately 10 Watts. This can be due, for example, to voltage or current limits in generator 100. However, other embodiments can deliver power that is close or substantially equal to the set power if the generator has, for example, higher voltage or current limits. The power settings described below are the power settings of the generator, unless otherwise indicated.

Initially, as illustrated by portion 510, probe 200 is operating in the ablative mode, and the ablation algorithm (404) causes generator 100 to produce a power level in accordance with, e.g., a substantially constant power setting (P-SET) on the generator (402). In another embodiment, the ablation algorithm causes generator 100 to produce power according to a dynamic control algorithm, such as a PID control algorithm. At line 515, probe 200 is determined to be operating in the non-ablative mode (406). The power control algorithm 400 then switches to the non-ablation algorithm (408) that causes generator 100 to produce a pulsed power level, as illustrated by portion 520. The pulsed power alternates between high power pulses (P-HI) having a duration of T-HI and low power pulses (P-LO) having a duration of T-LO, to limit the amount of energy delivered to tissue, and thus limit the amount of collateral cell death.

At some point in portion 520, for example, during one of the high power pulses as indicated by line 525, probe 200 is determined to be operating in the ablative mode (406). The power control algorithm then switches back to the ablation algorithm (404) that causes generator 100 to deliver power in accordance with the operator determined power setting (P-SET). The high power pulses of the non-ablation algorithm are sufficient in power and in duration to allow the probe to return to the ablative mode when, for example, the probe is positioned close to tissue. The power control algorithm 400 can be further configured to provide a quick return, e.g., within approximately 0 to 6.5 milliseconds, to the ablation algorithm when probe 200 returns to the ablative mode.

Figure 6:
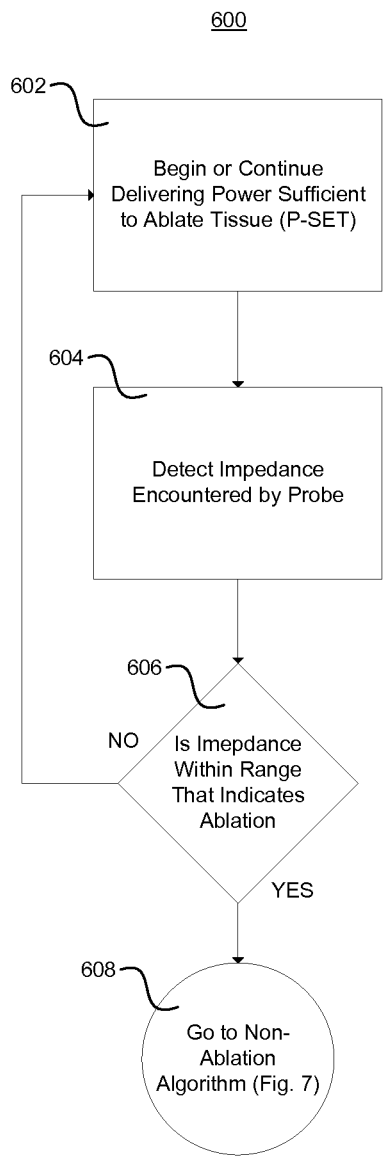
FIG. 6 is a flow chart showing an ablation algorithm of the power control method of FIG. 4.

Referring to FIG. 6, an ablation algorithm 600 controls power delivery when probe 200 is determined to be operating in the ablative mode. According to the ablation algorithm 600, a power setting (P-SET) is used to control the voltage and current to probe 200 to cause probe 200 to ablate the tissue (602). The power setting (P-SET) can be constant or variable and can be substantially equal to the setting inputted by an operator or can vary from the operator's setting. For example, P-SET may be between approximately 40 watts and approximately 300 Watts. Three exemplary values for P-SET (constant values of 60 W, 65 W, and 70 W) for use with the Glider probe are set forth below in Table 1. An exemplary value of P-SET for use with the Sculptor probe is a substantially constant value of approximately 150 Watts.

While continuing to deliver power sufficient to ablate tissue, the impedance encountered by probe 200 is periodically determined, e.g., between approximately every 1 millisecond and approximately every 10 milliseconds, by determining the voltage and the current across probe 200, to determine whether probe 200 is operating in the ablative mode (604). Each cycle of the algorithm that checks the impedance encountered by probe 200 is an "impedance check cycle." For the examples for the Glider probe set forth below in Table 1 and for the Sculptor probe, the duration of each impedance check cycle is approximately 6.5 milliseconds. The determined impedance is compared to a range of values, e.g., greater than a value between approximately 1000 ohms for the Glider probe and greater than approximately 700 ohms for the Sculptor probe, that have been determined to indicate when probe 200 is operating in the ablative and non-ablative modes (606). If the impedance is within this range of values ("no" branch from 606), then ablative power continues to be delivered to probe 200 (602). If the impedance drops below this range of values ("yes" branch from 606), it is determined that probe 200 is no longer ablating tissue, and generator 100 switches to a non-ablation algorithm (608).

The lower limit value of the range of impedance values used for comparison when switching from the ablation algorithm to the non-ablation algorithm (606) may be lower, by a margin, than the lower limit of the range that has been predetermined, as discussed above, to indicate that probe 200 is operating in the ablative mode. This lower value still indicates that the probe is operating in the ablative mode, but provides a hysteresis buffer before switching from the ablation algorithm to the non-ablation algorithm. For example, for the Glider probe, the lower limit of the impedance range that indicates operation in the ablative mode is approximately 1000 ohms, but the lower limit used for comparison when determining whether to switch from the non-ablation algorithm to the ablation algorithm is approximately 900 ohms. In another embodiment, for the Sculptor probe, the lower limit of the impedance range that indicates operation in the ablative mode is approximately 700 ohms, but the lower limit used for comparison when determining whether to switch from the non-ablation algorithm to the ablation algorithm is approximately 650 ohms.

The change from the ablation algorithm to the non-ablation algorithm occurs substantially immediately, e.g., within approximately 0 to 6.5 milliseconds, after the probe enters the non-ablative mode. The substantially immediate change is achieved because the delay in changing to the non-ablation algorithm is largely determined by the delay in determining that probe 200 is not ablating tissue, which is largely determined by the delay in measuring impedance. However, the impedance is measured frequently, e.g., approximately every 1 millisecond to approximately every 10 milliseconds, such as approximately every 6.5 milliseconds. The impedance can be determined at other regular or irregular intervals. Further, other embodiments can impose an additional delay in changing to the non-ablation algorithm in order, for example, to maintain a probe's ability to enter the ablative mode while a probe operator moves a probe from one tissue location to another and the probe momentarily moves to the non-ablative mode.

Figure 7:
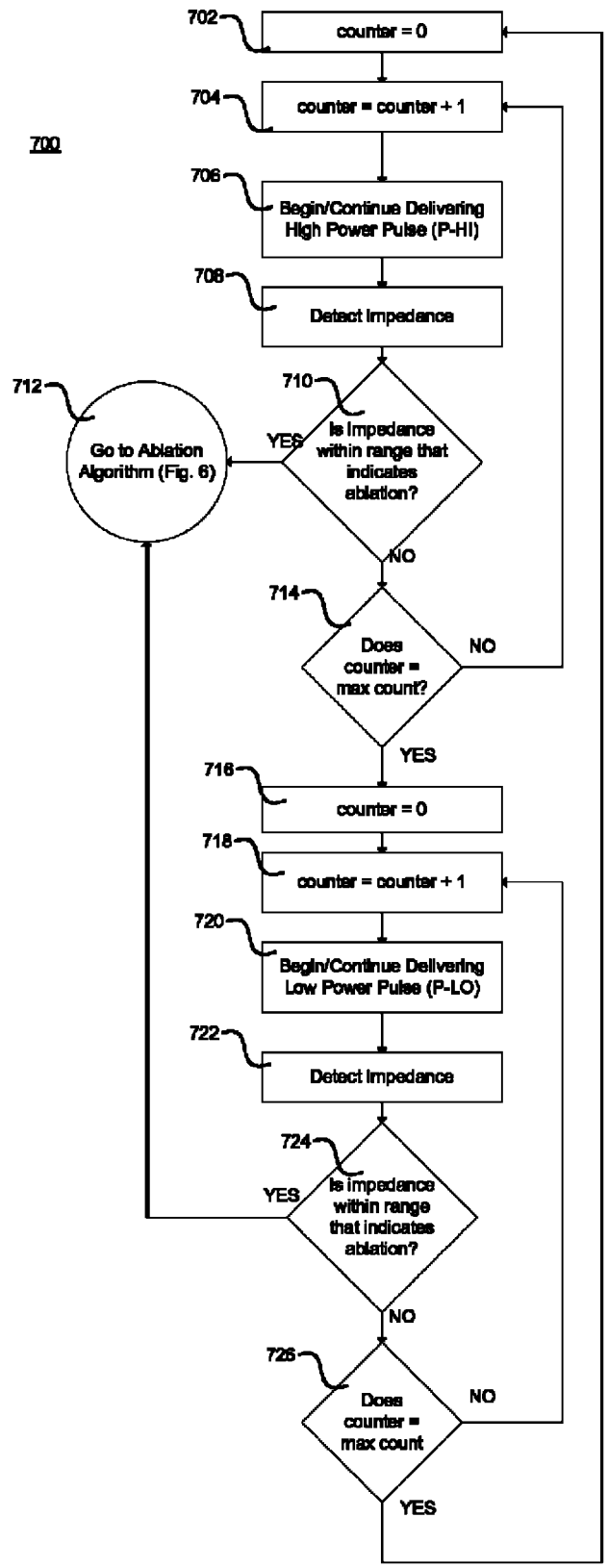
FIG. 7 is a flow chart showing a non-ablation algorithm of the power control method of FIG. 4.

Referring to FIG. 7, a non-ablation algorithm 700 controls the pulsed power delivered to probe 200 when probe 200 is determined to be operating in the non-ablative mode (608). To begin the high power portion of the pulsed power, a cycle counter is set to zero (702) and incremented by one (704). A high power setting (P-HI) is used to control voltage and/or current applied to probe 200 (706). The value of P-HI is sufficiently high so that probe 200 can operate in the ablative mode, e.g., approximately 40 watts to approximately 300 Watts. Exemplary values for P-HI for the three power settings of P-SET for the Glider probe are 60 Watts, 65 Watts, and 70 Watts, as set forth below in Table 1, and an exemplary value for P-HI for the power setting P-SET of 150 Watts for the Sculptor probe is approximately 150 Watts. While the exemplary values of P-HI are equal to the exemplary values of P-SET, the values of P-HI also could be greater than or less than the values of P-SET. That is, the high-power setting in the non-ablative mode's non-ablation algorithm 700 need not be the same as the power setting in the ablative mode's ablation algorithm 600, but can be higher or lower. Note that, if probe 200 is not ablating tissue, the actual power delivered to probe 200 can be close to the power setting of P-HI, e.g., 50 Watts delivered for a 60 Watt power setting. If probe 200 is ablating tissue, the actual power delivered can be lower than the setting of P-HI, due to the higher impedance, e.g., approximately 10 Watts delivered for a 60 Watt setting.

During the high power pulse, the impedance is determined, e.g., approximately every 1 millisecond to approximately every 10 milliseconds, by determining, e.g., the voltage and current across probe 200 (708). The determined impedance is compared to the predetermined impedance range that indicates ablation of tissue, e.g., greater than a value between approximately 50 ohms and approximately 4000 ohms (710). A value within this range indicates that probe 200 has switched from the non-ablative mode to the ablative mode. If the impedance is within this range ("yes" branch from 710), then generator 100 switches back to the ablation algorithm 600 described above (712).

When switching from the non-ablation algorithm to the ablation algorithm, the lower limit of the range used for comparison (710) may be higher, by a margin, than the lower limit of the impedance used for comparison when switching from the ablation algorithm to the non-ablation algorithm. The margin still indicates that the probe is operating in the ablative mode and provides a hysteresis buffer before switching from the non-ablation algorithm to the ablation algorithm. For example, for the Glider probe, the lower limit of the impedance is approximately 1000 ohms, but the lower limit value used for comparison when determining whether to switch from the ablation algorithm to the non-ablation algorithm is approximately 1100 ohms. In another embodiment, for the Sculptor probe, the lower limit of the impedance is approximately 700 ohms, but the lower limit value used for comparison when determining whether to switch from the ablation algorithm to the non-ablation algorithm is approximately 750 ohms.

If the impedance is not within the range ("no" branch from 710), non-ablation algorithm 700 checks whether the cycle counter has reached the maximum number of cycles for the high power portion of the algorithm (714). T-HI is equal to the maximum number of cycles multiplied by the length of each impedance determining cycle. T-HI is selected to be at least the minimum time necessary to allow probe 200 to enter the ablative mode, e.g., at least approximately 10 milliseconds, while limiting the amount of energy being delivered if probe 200 is operating in the non-ablative mode, e.g., approximately 100 milliseconds or less. Exemplary values of T-HI for the Glider probe (which are multiples of an exemplary impedance determining cycle of 6.5 milliseconds) are set forth below in Table 1. An exemplary value for T-HI for the Sculptor probe is approximately 30 milliseconds. If the number of cycles has not reached the maximum ("no" branch from 714), then generator 100 increments the cycle counter (704) and continues to use the P-HI setting to control power output to probe 200 (706). If the number of cycles has reached the maximum ("yes" branch from 714), generator 100 switches to the low power portion of non-ablation algorithm 700.

To begin the low power portion of the pulse, the cycle counter is reset to zero (716) and is incremented by one (718). A low power setting (P-LO) is used to control the amount of voltage and/or current applied to probe 200 (720). The value of P-LO is chosen so as to limit the amount of energy applied to tissue, and thus the amount of cell death, e.g., approximately 50 Watts or less, while still allowing probe 200 to easily switch back to P-HI with little or no ramp-up time, e.g., approximately 0 Watts or more. Exemplary values for P-LO are approximately 10 Watts for the Glider probe, as shown below in Table 1, and approximately 10 Watts for the Sculptor probe. Note that, because probe 200 is not ablating tissue, the actual power delivered to probe 200 typically will be close to the actual power setting of P-LO, e.g., approximately 3-5 Watts delivered for a 10 Watt power setting.

During the low power pulse, the impedance is determined, e.g., approximately every 1 millisecond to approximately 10 milliseconds, by determining, e.g., the voltage and current across probe 200 (722). The determined impedance is compared to the range of values that indicates the probe is ablating tissue, with or without an additional margin, as discussed above (724). If the impedance is within this range ("yes" branch from 724), probe 200 is switched back to the ablation algorithm (712). However, it can be unlikely that the impedance will be within this range during the low power pulse because power being delivered to probe 200 is typically too low for probe 200 to operate in the ablative mode. Thus, even if probe 200 is moved close enough to the tissue to ablate the tissue, probe 200 typically will remain in the non-ablative mode until the high power pulse (P-HI) is delivered to probe 200.

If the impedance is below the lower limit of this range ("no" branch from 724), non-ablation algorithm 700 checks whether the cycle counter has reached the maximum number of impedance check cycles for the low power portion of non-ablation algorithm 700 (726). T-LO is equal to the maximum number of impedance check cycles multiplied by the length of each cycle, and is selected to be, e.g., as long as possible so as to maximize the amount of time that P-LO is applied to the tissue to reduce cell death, e.g., between approximately 50 milliseconds and approximately 500 milliseconds. However, T-LO can also be limited so that non-ablation algorithm 700 switches to T-HI with sufficient frequency that there is substantially no noticeable delay, as perceived by the probe operator, in the probe switching to the ablative mode, e.g., approximately 0 to 6.5 milliseconds. Exemplary values of T-LO for the Glider probe (which are multiples of an exemplary impedance determining cycle of 6.5 milliseconds), as well as the average delay in returning to the ablative mode, are set forth below in Table 1. The average delay is equal to the average of T-HI and T-LO. An exemplary value of T-LO for the Sculptor probe is approximately 200 milliseconds.

Table 1 shows exemplary values for P-SET, P-HI, T-HI, P-LO, T-LO, and the average delay in change to ablative mode for generator settings of 60 Watts, 65 Watts, and 70 Watts for the design of the Glider probe. The average delay in change to the ablative mode are examples of delay times that cause no noticeable delay to the operator in switching from the non-ablative mode to the ablative mode. In contrast, embodiments for which T-LO is excessively long can cause a perceivable delay to a probe operator before the probe is allowed to change to ablative mode. Further, embodiments for which T-HI is too long can unnecessarily heat saline, whereas the values of T-HI in Table 1 are substantially the minimum sufficient to initiate delivery of power in the ablative mode.

TABLE 1

Exemplary Powers and Durations for Glider Probe

| P-SET (W) | P-HI (W) | T-HI (msec) | P-LO (W) | T-LO (msec) | Avg. Delay in Change to Ablative Mode (msec) |
|---|---|---|---|---|---|
| 60 | 60 | 19.5 (3 cycles) | 10 | 201.5 (21 cycles) | 120 msec |
| 65 | 65 | 26.0 (4 cycles) | 10 | 201.5 (21 cycles) | 127 msec |
| 70 | 70 | 32.5 (5 cycles) | 10 | 201.5 (21 cycles) | 133 msec |

If the number of cycles has not reached the maximum ("no" branch from 726), then generator 100 increments the cycle counter (718) and continues to use P-LO to control power output to probe 200 (720). If the number of cycles has reached the maximum ("yes" branch from 726), generator 100 switches to the high power portion of the non-ablation algorithm 700 (702-714). Generator 100 is able to increase to P-HI substantially instantaneously, e.g., within approximately 0 to 1 millisecond, at the end of T-LO, although in other embodiments there can be a more gradual ramp-up to P-HI.

Figure 8:
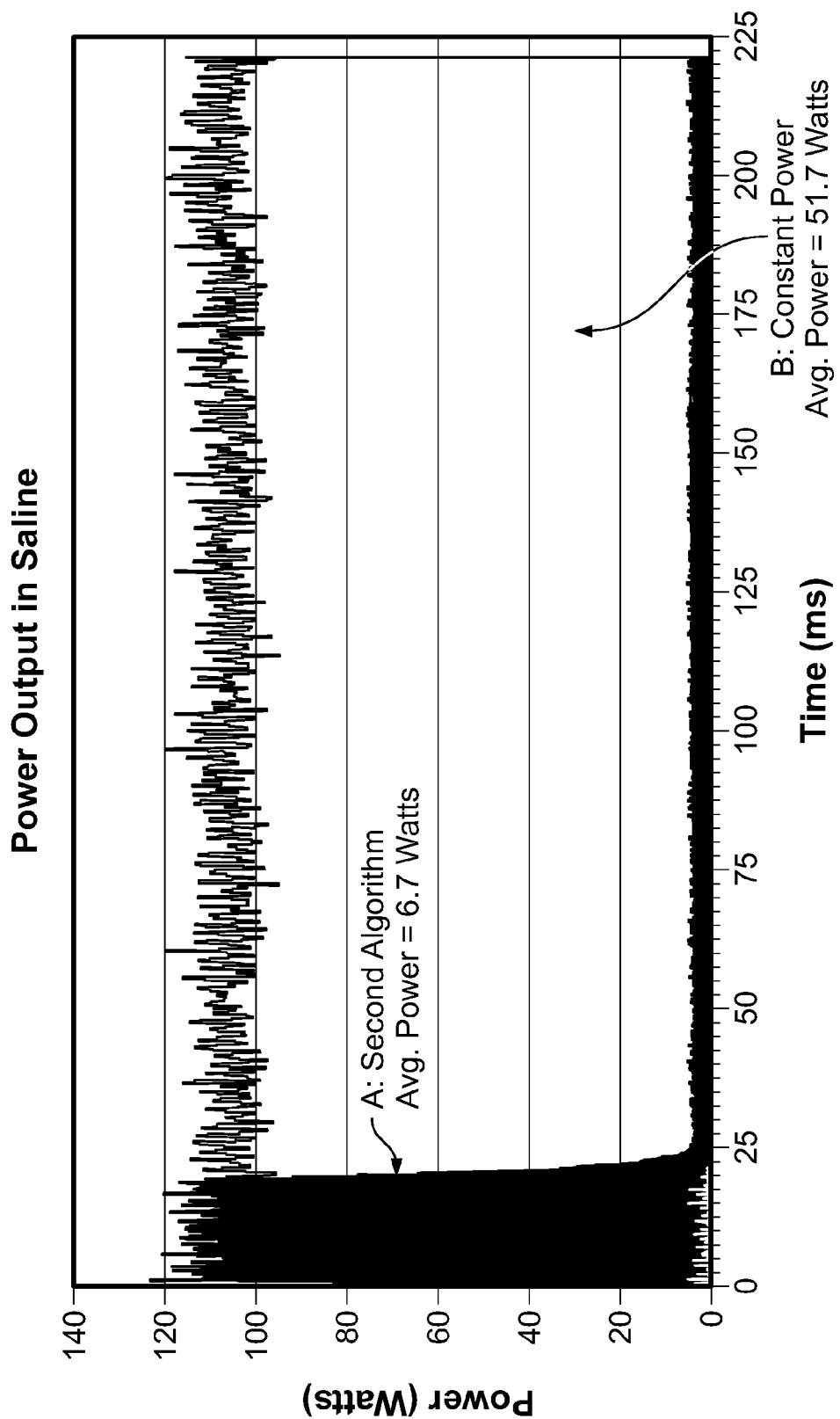
FIG. 8 is a graphical representation of the power output according to an embodiment of the non-ablation algorithm described in FIG. 7.

Referring to FIG. 8, the non-ablation algorithm 700 can result in a substantial reduction in overall power, and thus limit collateral cell death, during operation of probe 200 and, in particular, during the non-ablative mode. FIG. 8 shows the power output over time from a Glider probe operated according to one full cycle of non-ablation algorithm 700 (the darker colored plot indicated by A) and with a constant power setting for the same period of time (the lighter colored plot indicated by B) in saline solution with generator 100 power setting set to 60 Watts. The average power output according to the non-ablation algorithm 700 is approximately 6.7 Watts, while the average power output according to the constant power setting is approximately 51.7 Watts. Thus, the high and low power pulses of the non-ablation algorithm result in a reduction of power of approximately 87% as compared to a constant power setting.

As shown below in Table 2, experimental use of algorithm 400 on articular cartilage samples from a healthy bovine patella placed in room temperature saline showed average tissue necrosis being limited to less than 200 μm (average mean cell death of 108 μm and average maximum cell death of 167 μm) when power was applied according to algorithm 400 with a Glider probe positioned too far from the tissue to operate in the ablative mode. The articular cartilage was treated for 30 seconds at a power setting of 60 Watts while the power output and impedance were recorded. The experiment was performed three times with three different Glider probes. The average power output from the generator was approximately 7.3 Watts, an approximately 88% reduction from the 60 Watt setting. Each impedance measurement, and the average impedance, was less than 1000 ohms, indicating that the probe was operating in the non-ablative mode. The error for each value in Table 2 is plus or minus one standard deviation.

TABLE 2

| Probe | Mean cell death (μm) | Max cell death (μm) | Avg. Power (W) | Avg. Impedance (Ω) |
|---|---|---|---|---|
| 1 | 302 | 470 | 7 | 863 |
| 2 | 23 | 31 | 7 | 156 |
| 3 | 0 | 0 | 8 | 156 |
| Avg. | 108 | 167 | 7.3 | 392 |

The values set forth above are specific to the design of the Glider probe. Other types of probes, such as the Sculptor probe, and other types of treatments may need to be calibrated with different ranges of values of the parameter being measured and different values of P-SET, P-HI, T-HI, P-LO and/or T-LO.

Figure 9:
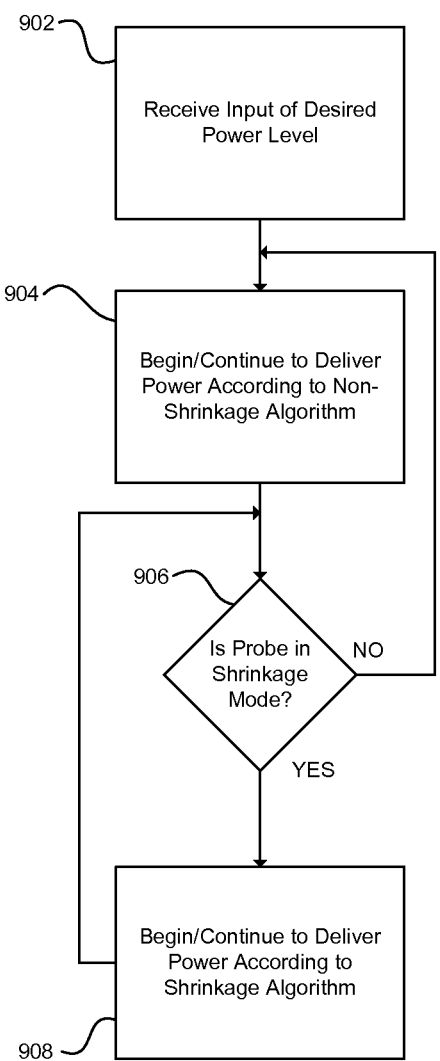
FIG. 9 is a flow chart showing another embodiment of the power control method of FIG. 1B used for shrinkage of tissue.
Figure 10:
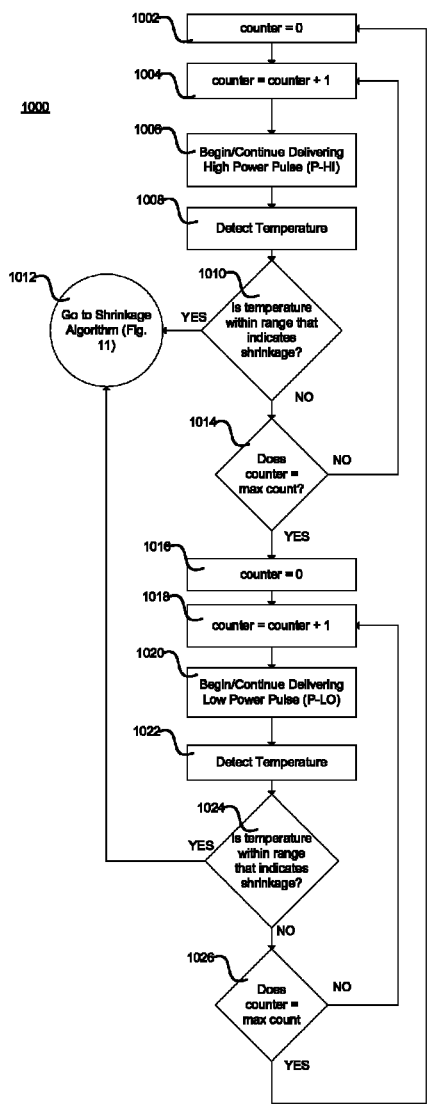
FIG. 10 is a flow chart showing a non-shrinkage algorithm of the power control method of FIG. 9.
Figure 11:
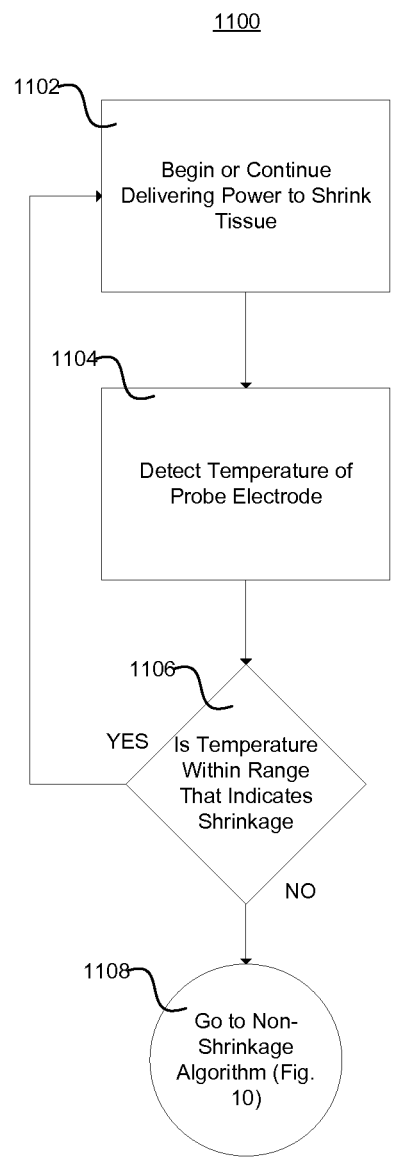
FIG. 11 is a flow chart showing a shrinkage algorithm of the power control method of FIG. 9.

Referring to FIGS. 9-11, in another embodiment, an algorithm 900 is used to control power delivery from generator 100 to a probe, based on the temperature of the probe electrode, in order to shrink tissue. The probe can be, for example, a TAC-S probe (catalog no. 7209633) or a mini-TAC-S probe (catalog no. 7209632), sold by Smith & Nephew, Inc. Tissue shrinkage occurs, for example, when the temperature of the tissue is between approximately 55° C. and approximately 100° C. When the temperature of the tissue is below or above this range, tissue does not shrink, and collateral tissue damage or death can occur. When the probe is not-shrinking tissue it is operating in the "non-shrinkage mode."

In an embodiment, shrinkage of tissue is indicated by a temperature of the probe electrode, e.g., between approximately 65° C. and approximately 90° C. The temperature range for the probe that indicates tissue shrinkage can vary based upon the generator power (P-SET) and temperature (Temp-SET) settings. The range of electrode temperature that indicates tissue shrinkage can be determined empirically for each probe, for example, by applying the probe to tissue samples, setting the generator to operate according to a dynamic control algorithm (e.g., according to a proportional-integral-derivative temperature control algorithm), and observing the temperature at which tissue shrinkage occurs.

The electrode temperature can vary based upon the probe design and configuration, and the power and temperature settings on the generator. For example, a probe having a larger surface area may have a narrower range of probe temperatures that achieve the tissue temperature required for shrinkage, because a larger mass electrode has a larger thermal mass, causing slower temperature changes in the probe electrode. In one embodiment, tissue shrinkage is indicated by a temperature of the TAC-S probe of approximately 75° C. to 85° C., with generator settings of approximately 20 Watts and approximately 75° C. In another embodiment, tissue shrinkage is indicated by a temperature of the mini-TAC-S probe of approximately 75° C. to 90° C., with generator settings of approximately 20 Watts and approximately 75° C. The temperature ranges that indicate tissue shrinkage may have lower limits that are less than the lower limits in these ranges and upper limits that are higher than the upper limits in these ranges.

The shrinkage mode typically occurs when the probe is placed sufficiently close to or in contact with the tissue surface, e.g., approximately 0 mm to approximately 5 mm from the tissue surface. When the probe is moved further away from the tissue surface, e.g., at least approximately 0.5 mm to at least approximately 5 mm, the probe typically operates in the "non-shrinkage mode." When the probe is close enough to the tissue to shrink the tissue and the temperature is within the range to shrink the tissue, the probe is operating in the "shrinkage mode." When the probe is further away from the tissue and/or the temperature is not within the range to shrink tissue, the probe is operating in the "non-shrinkage mode."

When the probe is close enough to tissue to operate in the shrinkage mode, the temperature of the electrode tends to rapidly reach the desired range of electrode temperatures that indicates tissue shrinkage, e.g., within approximately 1.5 seconds for the TAC-S probe and within approximately 1.0 seconds for the mini-TAC-S probe. When the probe is operating further from tissue, e.g., in the non-shrinkage mode, the temperature of the electrode tends to reach the desired temperature range that indicates shrinkage more slowly, if at all, e.g., approximately 10 seconds for the TAC-S probe and greater than 10 seconds, or not at all, for the mini-TAC-S probe. The time it takes the probe electrode to reach the shrinkage mode temperature range can be observed empirically by operating the probe at a constant power setting in saline and when applied to tissue, and determining the amount of time each takes to reach the shrinkage mode temperature range.

It is desirable to limit the amount of energy delivered to the probe when operating away from tissue and to determine when the probe is close enough to tissue to operate in the shrinkage mode. The temperature range that indicates operation in the shrinkage mode and the time that it takes the electrode to reach this temperature range in the shrinkage mode and in the non-shrinkage mode can be used to indicate whether the probe is operating in the shrinkage mode or the non-shrinkage mode, according to power control algorithm 900, described in greater detail below.

Referring to FIG. 9, power control algorithm 900 uses shrinkage and non-shrinkage algorithms to control the power to the probe. Generator 100 receives input of the desired power level from an operator of the probe (P-SET) (902). For example, as shown below in Table 3, the TAC-S probe uses a P-SET of approximately 20 Watts and the mini-TAC-S probe uses a P-SET of approximately 20 Watts. Generator 100 initially delivers power to the probe according to a non-shrinkage algorithm designed to limit the amount of power delivered to the tissue by delivering a pulsed power to the probe, as described in more detail below with respect to FIG. 10 (904). Algorithm 900 then periodically determines, while continuing to deliver power according to the non-shrinkage algorithm, whether the probe is delivering power in the shrinkage mode or the non-shrinkage mode (906). If the probe is operating in the non-shrinkage mode ("no" branch from 906), generator 100 continues to deliver power according to the non-shrinkage algorithm (904).

If the power control algorithm 900 determines that the probe is operating in the non-shrinkage mode ("yes" branch from 906), generator 100 switches to a shrinkage algorithm that is designed to deliver power in a manner that allows the probe to continue to operate in the shrinkage mode, as described in more detail below with respect to FIG. 11 (908). Algorithm 400 continues to periodically determine, while continuing to deliver power according to the shrinkage algorithm, whether the probe is operating in the shrinkage mode or the non-shrinkage mode (906) and quickly switches back to the non-shrinkage algorithm (904) upon a determination that the probe is operating in the non-shrinkage mode.

In certain instances, generator 100 may be controlled by the shrinkage algorithm even though the probe is operating in the non-shrinkage mode, e.g., if there is a lag in algorithm 900 determining that the probe has switched to the non-shrinkage mode. Conversely, in certain instances, generator 100 may be controlled by the non-shrinkage algorithm even though the probe is operating in the shrinkage mode, e.g., if there is a lag in algorithm 900 determining that the probe has switched to the shrinkage mode. Although the power control algorithm is depicted with the non-shrinkage algorithm being the initial setting, in another embodiment the shrinkage algorithm is the initial setting.

Referring to FIG. 10, a non-shrinkage algorithm 1000 controls pulsed power having portions of high power and portions of low power delivered to the probe when the probe is determined to be operating in the non-shrinkage mode (904). To begin the high power portion of the pulsed power, a cycle counter is set to zero (1002) and incremented by one (1004). A high power setting (P-HI) is used to control voltage and/or current applied to the probe so as to deliver a high power pulse (1006). The value of P-HI is sufficiently high so that the probe can reach the temperature range that indicates that the probe is close enough to tissue to operate in the shrinkage mode within the duration of T-HI. For example, as shown below in Table 3, the value of P-HI is approximately 40 Watts for the TAC-S probe and approximately 20 Watts for the mini-TAC-S probe. The values of P-HI also may be greater than, less than, or equal to the power setting on the generator.

During the high power pulse, the temperature of the probe electrode is determined, e.g., approximately every 1 millisecond to approximately every 100 milliseconds, by a thermocouple located within the probe (1008). Each cycle of determining temperature is a "temperature determining cycle." The determined temperature is compared to a range of temperatures that indicates shrinkage of tissue, e.g., between approximately 75° C. and approximately 85° C. for the TAC-S probe and between approximately 75° C. and approximately 90° C. for the mini-TAC-S probe (1010).

If the temperature is within this range ("yes" branch from 1010), then generator 100 switches to a shrinkage algorithm 1100 described below (1012). In an embodiment, the lower limit of the range used for comparison to the temperature of the probe is greater than the lower limit of the range that indicates shrinkage of tissue, by a margin, e.g., approximately 2° C., to provide a hysteresis buffer before switching from the non-shrinkage algorithm to the shrinkage algorithm. For example, generator 100 switches from the non-shrinkage algorithm 1000 to the shrinkage algorithm 1100 when the temperature is between approximately 77° C. and approximately 85° C. for the TAC-S probe, and between approximately 77° C. and approximately 90° C. for the mini-TAC-S probe.

If the temperature is not within the range ("no" branch from 1010), non-shrinkage algorithm 1000 checks whether the cycle counter has reached the maximum number of cycles for the high power portion of the algorithm (1014). If the number of cycles has not reached the maximum ("no" branch from 1014), then generator 100 increments the cycle counter (1004) and continues to use the P-HI setting to control power output to the probe (1006). If the number of cycles has reached the maximum ("yes" branch from 1014), generator 100 switches to the low power portion of non-shrinkage algorithm 1000.

The duration of the high power pulse (T-HI) is equal to the maximum number of cycles multiplied by the length of each temperature determining cycle. T-HI is greater than the time period required for the probe to reach the desired temperature range when shrinking tissue, and less than the time period required for the probe to reach the desired temperature range when not shrinking tissue, which is determined as described above. For example, for the TAC-S probe, T-HI is approximately 2 seconds, which is greater than the time required for the TAC-S probe to reach the desired temperature range when shrinking tissue (e.g., approximately 0.5 seconds to 1.5 seconds) but less than the time required to reach the temperature range when not shrinking tissue (e.g., greater than approximately 10 seconds). Similarly, for the mini-TAC-S probe T-HI is approximately 1.5 seconds, which is greater than the time required for the mini-TAC-S probe to reach the desired temperature range when shrinking tissue (e.g., approximately 0.5 seconds to 1 second) but less than the time required to reach the temperature range when not shrinking tissue (e.g., greater than approximately 10 seconds). Thus, algorithm 1000 switches to the low power pulse if the probe has not reached the temperature that indicates shrinkage within the time period of T-HI, and switches to the shrinkage algorithm if the probe has reached the temperature that indicates shrinkage within the time period of T-HI. In this way, algorithm 1000 is able to make a determination as to whether the probe is shrinking tissue.

To begin the low power portion of the pulse, the cycle counter is reset to zero (1016) and is incremented by one (1018). A low power setting (P-LO) is used to control the amount of voltage and/or current applied to the probe to deliver a low power pulse (1020). The value of P-LO is chosen so as to limit the amount of energy applied to tissue, and thus the amount of cell death, e.g., approximately 5 Watts or less for the TAC-S and the mini-TAC-S probes, while still allowing the probe to easily switch back to P-HI with little or no ramp-up time. During the low power pulse, the temperature of the electrode is determined, e.g., approximately every 1 millisecond to approximately 10 milliseconds (1022). The determined temperature is compared to the range of values that indicates the probe is shrinking tissue, as discussed above (1024). If the temperature is within this range ("yes" branch from 1024), the probe is switched to the shrinkage algorithm (1012). However, it can be unlikely that the temperature will be within this range during the low power pulse because power being delivered to the probe is typically too low for the probe to achieve the temperature range. Thus, even if the probe is moved close to the tissue, the probe typically will remain in the non-shrinkage mode until the high power pulse (P-HI) is delivered to the probe.

If the temperature is below the lower limit of this range ("no" branch from 1024), non-shrinkage algorithm 1000 checks whether the cycle counter has reached the maximum number of temperature check cycles for the low power portion of non-shrinkage algorithm 1000 (1026). T-LO is equal to the maximum number of impedance check cycles multiplied by the length of each cycle, and is selected to be, e.g., as long as possible so as to maximize the amount of time that P-LO is applied to the tissue to reduce cell death, e.g., between approximately 1 second and approximately 3 seconds. For example, T-LO is approximately 2 seconds for the TAC-S and the mini-TAC-S probes.

If the number of cycles has not reached the maximum ("no" branch from 1026), then generator 100 increments the cycle counter (1018) and continues to use P-LO to control power output to the probe (1020). If the number of cycles has reached the maximum ("yes" branch from 1026), generator 100 switches to the high power portion of the non-shrinkage algorithm 1000 (1002-1014). Generator 100 is able to increase to P-HI substantially instantaneously, e.g., within approximately 0 to 1 millisecond, at the end of T-LO, although in other embodiments there can be a more gradual ramp-up to P-HI.

Referring to FIG. 11, a shrinkage algorithm 1100 controls power delivery when the probe is determined to be operating in the shrinkage mode. According to the shrinkage algorithm 1100, power is delivered to the probe according to, e.g., a dynamic control algorithm, based on the power setting on the generator (P-SET) (1102). In one embodiment, the dynamic control algorithm is a known proportional-integral-derivative (PID) temperature control algorithm that attempts to maintain the probe electrode temperature within the desired temperature range, e.g., between approximately 75° C. and approximately 85° C. for the TAC-S probe and between approximately 75° C. and approximately 90° C. for the mini-TAC-S probe. In other embodiments, the dynamic control algorithm can be a constant or variable power output and can be substantially equal to the setting inputted by an operator or can vary from the operator's setting.

While continuing to deliver power according to the dynamic control algorithm, the temperature of the probe electrode is also periodically determined by algorithm 1100, e.g., between approximately every 1 millisecond and approximately every 10 milliseconds, to determine whether the probe is operating in the shrinkage mode (1104). For example, the temperature is determined approximately every 6.5 milliseconds. The determined temperature is compared to the desired range of temperature values, as described above, that have been determined to indicate when the probe is operating in the shrinkage and non-shrinkage modes (1106). If the temperature is within this range of values ("yes" branch from 1106), then power continues to be delivered to the probe according to the temperature control algorithm (1102). If the temperature is outside this range of values ("no" branch from 1106), it is determined that the probe is no longer shrinking tissue, and generator 100 switches to a non-shrinkage algorithm (1108).

In an embodiment, the lower limit of the range used for comparison to the temperature of the probe is less than the lower limit of the range that indicates shrinkage of tissue, by a margin, e.g., of approximately 2° C. These lower limits still indicate that the probe is shrinking tissue and provide a hysteresis buffer before switching from the shrinkage algorithm to the non-shrinkage algorithm. For example, generator 100 switches to the shrinkage algorithm 1100 when the temperature is between approximately 73° C. and approximately 85° C. for the TAC-S probe, and between approximately 73° C. and approximately 90° C. for the mini-TAC-S probe.

If the temperature is below this range of values, the change from the shrinkage algorithm to the non-shrinkage algorithm occurs substantially immediately, e.g., within approximately 0 to 1 millisecond, after the algorithm determines that the temperature is below the range of values. The substantially immediate change is achieved because the delay in changing to the non-shrinkage algorithm is largely determined by the delay in determining that the probe is not shrinking tissue, which is largely determined by the delay in measuring temperature. However, the temperature is measured frequently, e.g., approximately every 1 millisecond to approximately every 10 milliseconds, such as approximately every 6.5 milliseconds. The temperature can be determined at other regular or irregular intervals. Further, other embodiments can impose an additional delay in changing to the non-shrinkage algorithm in order, for example, to maintain a probe's ability to enter the shrinkage mode while a probe operator moves a probe from one tissue location to another and the probe momentarily moves to the non-shrinkage mode. If the temperature is above this range of values, generator 100 can shut off power delivery to the probe completely for a period of time to allow the tissue to cool before switching to the non-shrinkage algorithm. In other embodiments, generator 100 can require the user to manually restart power delivery to the probe after shutting off power, can perform other algorithms, and can have a hysteresis buffer at the upper limit of the temperature range.

Table 3 shows exemplary values for the temperature setting on the generator (Temp-SET), the temperature range that indicates shrinkage (Temp Range), the power setting on the generator (P-SET), the power setting for the high power portion of the pulsed power (P-HI), the duration of the high power pulse (T-HI), the power setting for the low power portion of the pulsed power (P-LO), and the duration of the low power portion of the pulse (T-LO) for embodiments of the algorithm 900 using the TAC-S probe and the mini-TAC-S probe.

TABLE 3

Exemplary Values for TAC-S Probe and Mini-TAC-S Probe

| | TAC-S Probe | Mini-TAC-S Probe |
|---|---|---|
| Temp-SET | 75° C. | 75° C. |
| Temp Range | 75° C. to 85° C. | 75° C. to 90° C. |
| P-SET | 20 Watts | 20 Watts |
| P-HI | 40 Watts | 20 Watts |
| P-LO | 5 Watts | 5 Watts |
| T-HI | 2 seconds | 1.5 seconds |
| T-LO | 2 seconds | 2 seconds |

In another embodiment for delivering energy to a probe to shrink tissue, the rate at which the probe's temperature approaches the range of temperatures that indicates shrinkage of tissue, as described above with respect to algorithm 900, is used to determine whether the probe is close enough to tissue to be shrinking the tissue. While delivering power according to a constant power setting of the generator, the rate at which the temperature of the probe approaches the range of temperatures that indicate shrinkage is determined, e.g., by computing a derivative of the probe temperature with respect to time.

The rate of temperature increase is compared to a range of rates. The range of rates has been predetermined to indicate whether the probe is close enough to tissue to shrink the tissue at, for example, a temperature within the range of temperatures. A slower rate indicates that the probe is positioned too far from the tissue to shrink the tissue. A faster rate indicates that the probe is positioned close enough to tissue to shrink tissue. If the rate is outside of the predetermined range of rates, the generator delivers power according to the pulsed mode of the non-shrinkage algorithm 1000, as described above. If the rate is within the range of rates, the generator delivers power according to the shrinkage algorithm 1100 described above.

The range of rates can vary based upon several factors, including probe design and generator settings. In one embodiment, for a TAC-S probe operating at a power setting of 20 Watts and a temperature setting of 75° C., the range of rates that indicates that the probe is positioned close enough to tissue to initiate or sustain shrinkage is above approximately 20° C./second. In another embodiment, for a mini-TAC-S probe operating at a power setting of 10 Watts and a temperature setting of approximately 75° C., the range of rates that indicates that the probe is positioned close enough to tissue to initiate or sustain shrinkage is above approximately 40° C./second. In certain embodiments, the range of rates determined for one probe design can be used for a different probe design. In another embodiment, the rate can be continuously monitored, and the generator can switch between the shrinkage algorithm and the non-shrinkage algorithm based on the rate of temperature change.

In another embodiment, an algorithm analogous to algorithm 900 can be used to control power output to a probe, e.g., a TAC-S probe, to shrink tissue, based upon monitoring the impedance encountered by the probe. Initially, the probe delivers a power according to a dynamic control algorithm, such as a temperature PID dynamic control algorithm, to a probe, such as the TAC-S probe, sufficient to shrink tissue. The algorithm then periodically determines the impedance encountered by the probe and compares the impedance to a range of impedance values that has been predetermined to indicate that the probe is shrinking tissue. The impedance encountered by the probe will increase as the tissue shrinks. If the impedance is within the range of impedance values that indicates the probe is shrinking tissue, the algorithm continues to deliver power to the probe according to the dynamic control algorithm. If the impedance is greater than the upper limit of the range, the algorithm causes the generator to switch to a pulsed power setting. During delivery of the pulsed power setting, the algorithm continues to monitor the impedance encountered by the probe. If the impedance is still greater than the upper limit of the range, the algorithm continues to deliver the pulsed power to the probe. If the impedance decreases to be within the range that indicates shrinkage of tissue, the algorithm causes the generator to switch back to the dynamic control algorithm.

A number of embodiments have been described. Nevertheless, it will be understood that various modifications may be made. The algorithm can be configured for use with other types of probes having a variety of shapes and sizes and in a variety of types of procedures. For example, the algorithm can be used with the following probes manufactured by Smith & Nephew, Inc., in the following procedures: the Glider probe for use in thermal chondroplasty in the knee, hip, shoulder, or hand; the Sculptor, Ablator (catalog no. 7209654), or Saphyre (catalog no. 7209686) probe for use in subacromial decompression in the shoulder, meniscectomy in the knee, or synovectomy in the shoulder, knee, wrist, ankle, hip, elbow, or hand; or a Ligament Chisel (catalog no. 7209649) for use in triangular fibrocartilage complex (TFCC) debridement or carpal tunnel release in the wrist. A single probe can be used for multiple treatment modes using different algorithms.

Parameters other than impedance and temperature, such as voltage, current, or power, can be monitored in order to determine whether the probe is operating in the desired manner, or whether to switch between algorithms. Two or more parameters can be determined together to determine whether the probe is operating in the desired mode of operation. The desired range of values for the parameter can be closed ended or open ended. The algorithm used when operating in the desired manner (e.g., the ablative mode) can have a constant or a variable output and can have its own dynamic control algorithm, such as a PID controller. The pulsed power algorithm used when the probe is not operating in the desired manner (e.g., the non-ablative mode) can be pulsed to more than two power levels or can have a waveform, such as a sinusoidal wave. The parameter (e.g., impedance) can be monitored more or less frequently. The values of P-SET, P-HI, T-HI, P-LO, and T-LO can be higher or lower to achieve other objectives. The time for T-HI or T-LO can be counted in a different way such as by using a separate timing circuit. In addition to or instead of changing power output, the operator can be notified of, e.g., the non-ablative mode or non-shrinkage mode by, for example, an audible alarm, a visual display, or complete shutdown of the system. The algorithms can be used to control, e.g., power, current, and/or voltage delivered to the probe.

The impedance, voltage, current, temperature, or other parameters, can be monitored for other reasons, such as to determine whether the probe is stationary for an undesired period of time. For example, if the impedance rises above a threshold amount, indicating a stationary probe, the power to the probe can be shut off and the operator can be required to manually reinitiate ablation. In addition or in the alternative, the operator can be warned by an audible alarm or a visual indication.

Implementations may include one or more devices configured to perform one or more processes. A device may include, for example, discrete or integrated hardware, firmware, and software. Implementations may be embodied in a processing device, such as, for example, a processor, a microprocessor, an integrated circuit, or a programmable logic device. Implementations also may be embodied in a device, such as, for example, a volatile or non-volatile memory structure, such as, for example, a hard disk, a flash memory, a compact diskette, a random access memory, and a read-only memory. The memory structure may include one or more computer readable media having instructions for carrying out one or more processes. The computer readable media may include, for example, magnetic or optically-readable media, and formatted electromagnetic waves encoding or transmitting instructions. Instructions may be, for example, in hardware, firmware, software, or in an electromagnetic wave. A processing device may include, therefore, a device configured to carry out a process, or a device including computer readable media having instructions for carrying out a process.

These and other embodiments are within the scope of the following claims.

What is claimed is:

1. A method comprising:
    determining whether a probe is delivering power in an ablative mode or a non-ablative mode;
    delivering power to the probe according to a first algorithm when in the ablative mode;
    delivering power to the probe according to a second algorithm different from the first algorithm when in the non-ablative mode, the second algorithm comprising a pulsed profile including portions of low power and portions of high power, the high power portions for initiating the ablative mode.

2. The method of claim 1 further comprising limiting the portions of low power to a duration that causes substantially no noticeable delay in initiating ablation.

3. The method of claim 1 wherein the duration of the portions of low power is between approximately 50 milliseconds and approximately 500 milliseconds.

4. The method of claim 1 wherein the portions of low power comprise power between approximately 0 watts and approximately 50 watts.

5. The method of claim 1 wherein the portions of high power have a duration substantially equal to a minimum length sufficient to initiate ablation.

6. The method of claim 1 wherein the portions of high power comprise power between approximately 40 watts and approximately 300 watts.

7. An apparatus comprising:
    an electrosurgical probe configured to deliver power to tissue; and
    a control module configured to:
        determine whether the probe is delivering power in an ablative mode or a non-ablative mode,
        deliver power to the probe according to a first algorithm when in the ablative mode; and
        deliver power to the probe according to a second algorithm different from the first algorithm when in the non-ablative mode, wherein the second algorithm comprises a pulsed profile including delivering power to the probe at each occurrence of portions of low power and portions of high power, the high power portions for initiating the ablative mode.

8. The apparatus of claim 7 wherein the control module is configured to limit the portions of low power to a duration that causes substantially no noticeable delay in initiating ablation.

9. The apparatus of claim 8 wherein the duration of the portions of low power is between approximately 50 milliseconds and approximately 500 milliseconds.

10. The apparatus of claim 9 wherein the portions of low power comprise power between approximately 0 watts and approximately 50 watts.

11. The apparatus of claim 9 wherein the control module is configured to providing the portions of high power with a duration substantially equal to a minimum length sufficient to initiate ablation.

12. The apparatus of claim 9 wherein the portions of high power comprise power between approximately 40 watts and approximately 300 watts.

* * * * *